United States Patent
Hefetz et al.

(10) Patent No.: US 10,517,557 B2
(45) Date of Patent: Dec. 31, 2019

(54) SYSTEMS AND METHODS FOR MOLECULAR BREAST IMAGING

(71) Applicant: General Electric Company, Schenectady, NY (US)

(72) Inventors: Yaron Hefetz, Kibbutz Alonim (IL); Nurit Rivka Wartski, Zichron Yaakov (IL); Pavel Livshits, Haifa (IL); Jonathan Sachs, Haifa (IL)

(73) Assignee: General Electric Company, Schenectady, NY (US)

( * ) Notice: Subject to any disclaimer, the term of this patent is extended or adjusted under 35 U.S.C. 154(b) by 779 days.

(21) Appl. No.: 15/187,077

(22) Filed: Jun. 20, 2016

(65) Prior Publication Data

US 2017/0360388 A1 Dec. 21, 2017

(51) Int. Cl.
| | |
|---|---|
| *A61B 6/00* | (2006.01) |
| *A61B 6/12* | (2006.01) |
| *A61B 6/04* | (2006.01) |
| *A61B 18/00* | (2006.01) |
| *A61B 10/04* | (2006.01) |
| *A61B 18/02* | (2006.01) |
| *A61B 18/12* | (2006.01) |

(52) U.S. Cl.
CPC ............. *A61B 6/502* (2013.01); *A61B 6/04* (2013.01); *A61B 6/12* (2013.01); *A61B 6/4258* (2013.01); *A61B 6/463* (2013.01); *A61B 6/468* (2013.01); *A61B 6/5217* (2013.01); *A61B 6/5282* (2013.01); *A61B 18/02* (2013.01); *A61B 18/12* (2013.01); *A61B 2010/045* (2013.01); *A61B 2018/00577* (2013.01)

(58) Field of Classification Search
CPC ....... A61B 6/502; A61B 6/4258; A61B 6/463; A61B 6/5217; A61B 6/5282; A61B 6/12; A61B 6/04; A61B 6/468; A61B 18/12; A61B 2018/00577; A61B 2010/045; A61B 18/02
See application file for complete search history.

(56) References Cited

U.S. PATENT DOCUMENTS 5,625,191 A * 4/1997 Nakamura ............. A61B 6/102
  250/363.02
5,732,704 A * 3/1998 Thurston ............... A61B 6/4258
  250/336.1

(Continued)

OTHER PUBLICATIONS

Dorbala et al., Single Photon Emission Computed Tomography (SPECT) Myocardial Perfusion Imaging Guidelines: Instrumentation, Acquisition, Processing, and Interpretation, ASNC SPECT Imaging Guidelines, Journal of Nuclear Cardiology, vol. 25, No. 5;1784-1846, Sep./Oct. 2018.*

(Continued)

*Primary Examiner* — Bo Joseph Peng

(74) *Attorney, Agent, or Firm* — McCoy Russell LLP

(57) ABSTRACT

Methods and systems are provided for molecular breast imaging. In one embodiment, a method for nuclear medicine imaging comprises: during an acquisition of emission data from an anatomy of interest, calculating an average counts per pixel in non-target tissue; and responsive to the average counts per pixel reaching a threshold, automatically stopping the acquisition. In this way, an amount of time spent by a patient undergoing an MBI procedure is optimized for the patient.

14 Claims, 13 Drawing Sheets

(56) References Cited

U.S. PATENT DOCUMENTS

| | | | |
|---|---|---|---|
| 6,670,449 B1* | 12/2003 | Miesenbock | C07K 14/43595 530/350 |
| 8,115,171 B2 | 2/2012 | Blevis | |
| 8,200,316 B2 | 6/2012 | Keppel et al. | |
| 8,923,952 B2 | 12/2014 | O'Connor et al. | |
| 2005/0053190 A1* | 3/2005 | Gohno | A61B 6/032 378/16 |
| 2007/0081721 A1* | 4/2007 | Xiao | G06T 5/009 382/167 |
| 2009/0304582 A1* | 12/2009 | Rousso | A61B 5/02755 424/1.61 |
| 2011/0268339 A1 | 11/2011 | Volokh et al. | |
| 2015/0238167 A1* | 8/2015 | Lall | A61B 8/4416 600/424 |
| 2015/0262389 A1* | 9/2015 | Li | G01T 1/1603 382/131 |
| 2017/0319155 A1* | 11/2017 | Rubenstein | A61B 6/037 |

OTHER PUBLICATIONS

Madsen, Computer Acquisition of Nuclear Medicine Images, Journal of Nuclear Medicine Technology, vol. 22, No. 1, Mar. 1994.*

Shirazu et al., Evaluating the effect of acquisition parameters on image quality and acquisition time with SPECT using LEHR collimator, International Journal of Scientific & Engineering Research, vol. 4, Issue 9, Sep. 2013.*

Sitek, Data analysis in emission tomography using emission-count posteriors, Phys. Med. Biol. 57, 6779-6795, 2012.*

Harris, C. et al., "Tc-99m attenuation coefficients in water-filled phantoms determined with gamma cameras," Medical Physics, vol. 11, No. 5, Sep. 1984, 5 pages.

Attix, F., "Handout Summarizing Chapter 3: Exponential Attenuation, from Book Entitled 'Introduction to Radiological Physics and Radiation Dosimetry'," Wiley-VCH, Jan. 1991, 8 pages.

Bright, D. et al., "Visibility of objects in computer simulations of noisy micrographs," Journal of Microscopy, vol. 189, Pt. 1, Jan. 1998, 18 pages.

Siegel, J. et al., "MIRD Pamphlet No. 16: Techniques for Quantitative Radiopharmaceutical Biodistribution Data Acquisition and Analysis for Use in Human Radiation Dose Estimates," Journal of Nuclear Medicine, vol. 40, No. 2, Feb. 1999, 25 pages.

"Thyroid Uptake Index Protocol for Xeleris Functional Imaging P&R Systems Operator Guide," GE Healthcare Technical Publication, Revision 2, Mar. 2010, 42 pages.

* cited by examiner

SYSTEMS AND METHODS FOR MOLECULAR BREAST IMAGING

FIELD

Embodiments of the subject matter disclosed herein relate to nuclear medicine (NM) imaging systems, and more particularly, to molecular breast imaging (MBI) systems.

BACKGROUND

Molecular breast imaging (MBI) typically involves the injection of a radiotracer into a patient wherein the radiotracer is carried by the bloodstream throughout the patient's body while emitting high-energy gamma photons which can be detected by a detection and imaging system, such as a system of cadmium zinc tellurium (CZT)-based detectors. Nuclear imaging systems (also called molecular imaging systems) work by detecting the distribution of gamma ray emanations throughout the patient's body or from within a specific region of interest (ROI). Areas where the gamma ray emanations are remarkably higher than would be the case for normal tissue at that area indicate an increased amount of uptake of the radiotracer in that tissue, possibly indicating cancerous tissue, while areas where the gamma ray emanations are remarkably lower than would be the case for normal tissue at that area indicate a decreased amount of uptake of radiotracer in that tissue area, possibly indicating necrotic or dead tissue. Thus, MBI utilizes nuclear/molecular imaging focused on the breast and surrounding ROIs (e.g., the axillary lymph nodes), primarily to detect or screen for breast cancer.

In conventional MBI workflows, it can take a long time to gather sufficient gamma photon counts to produce a suitable image. Typically, an acquisition or scan runs for a predetermined amount of time while the imaging system accumulates gamma photon counts. After the predetermined amount of time elapses, the imaging system stops accumulating gamma photon counts. One approach for reducing the amount of time that an acquisition or scan takes includes displaying an image of the photon counts as they accumulate. An operator of the imaging system can stop the acquisition when he or she decides that a sufficient amount of emission data is accumulated. Such an approach is based on the subjective qualitative evaluation of the image by the operator. It would be desirable, therefore, to provide a quantitative method for evaluating the sufficiency of accumulated emission data for diagnostic purposes.

BRIEF DESCRIPTION

In one embodiment, a method for nuclear medicine imaging comprises, during an acquisition of emission data from an anatomy of interest, calculating an average counts per pixel in non-target tissue, and, responsive to the average counts per pixel reaching a threshold, automatically stopping the acquisition. In this way, an amount of time spent by a patient undergoing an MBI procedure is optimized for the patient.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 6:
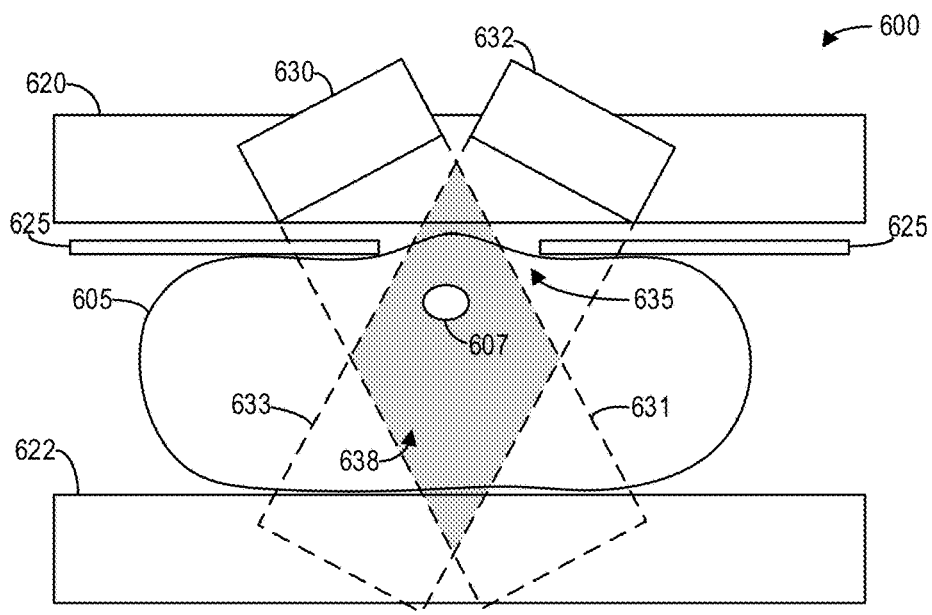
FIG. 6-7 show schematic diagrams illustrating example configurations of biopsy detectors in accordance with an embodiment.
Figure 7:
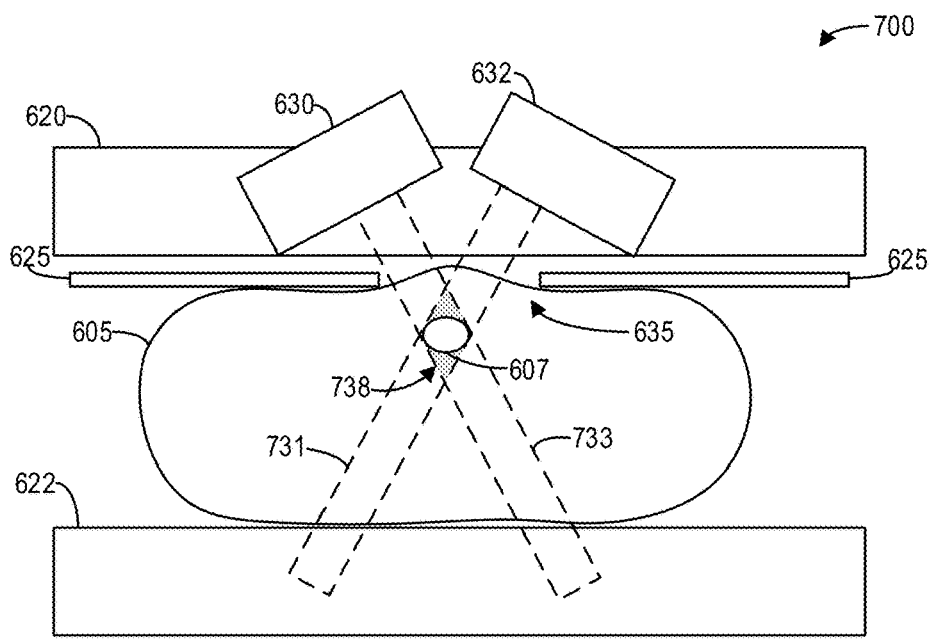
Figure 8:
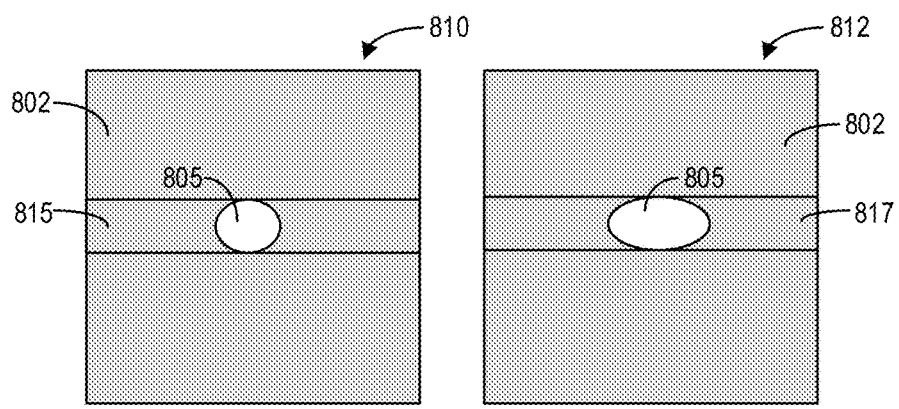
FIG. 8 shows example images acquired using biopsy detectors.
Figure 10:
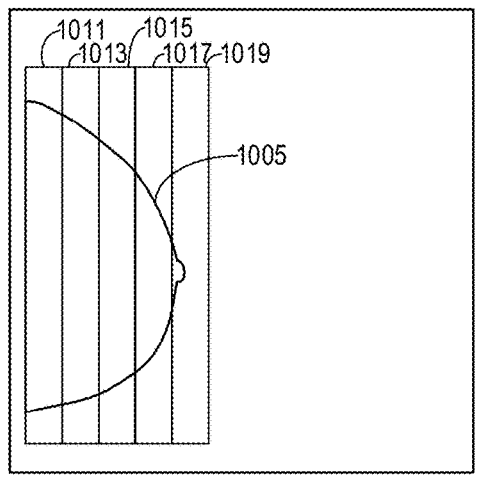
FIG. 10 shows an example image of an anatomy of interest and a graph illustrating photon energy levels corresponding to slices of the example image.
Figure 10:
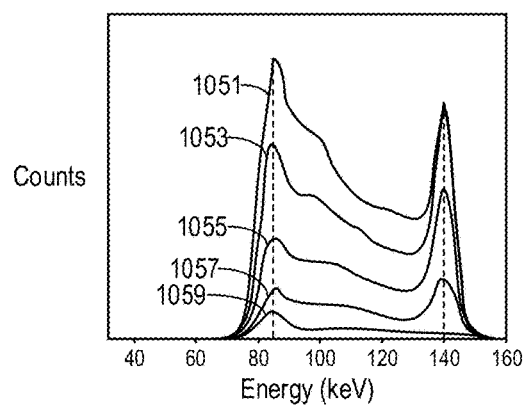
Figure 11:
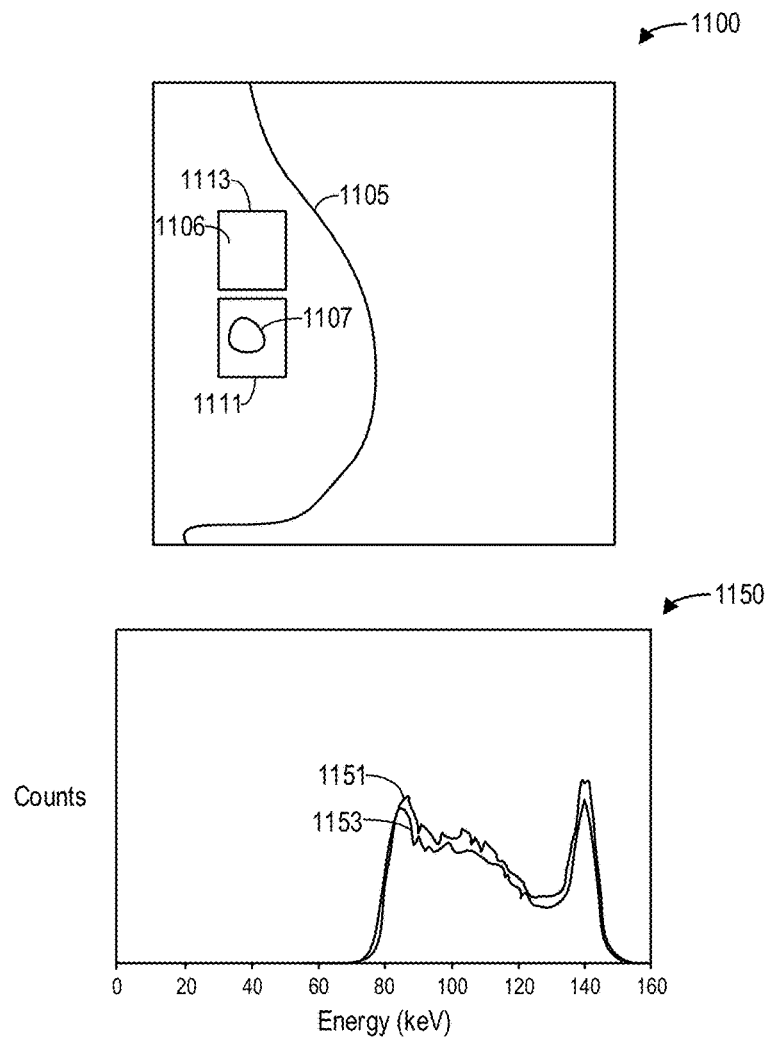
FIG. 11 shows an example image of an anatomy of interest and a graph illustrating energy levels corresponding to selected regions of the example image in accordance with an embodiment.
Figure 12:
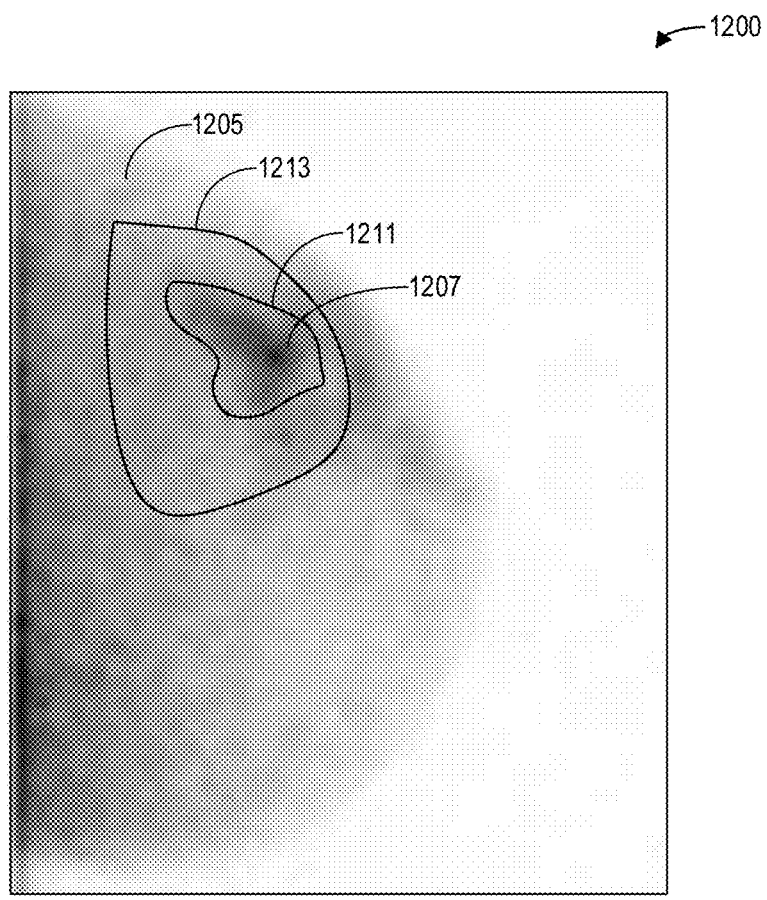
FIG. 12 shows an example image with selected regions for attenuation correction in accordance with an embodiment.
Figure 13:
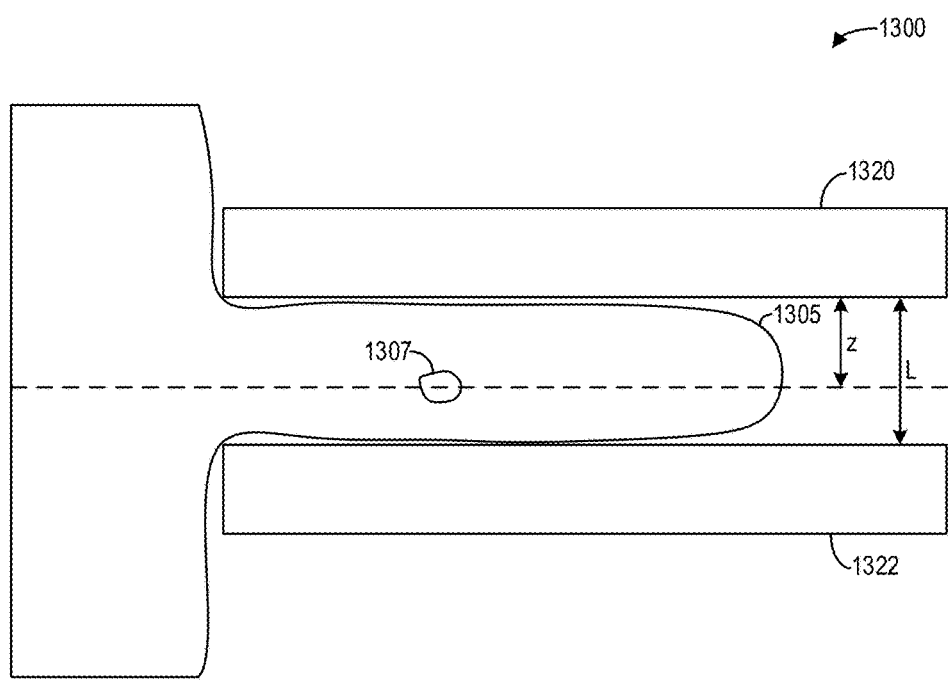
FIG. 13 shows a schematic diagram illustrating aspects of the imaging system of FIGS. 1-3 pertaining to attenuation correction in accordance with an embodiment.

The following description relates to various embodiments of a nuclear medicine imaging system. In particular, systems and methods are provided for molecular breast imaging (MBI). A system for MBI, such as the molecular imaging system depicted in FIGS. 1-3, includes two gamma cameras coupled to a gantry. An anatomy of interest, such as a breast, may be positioned between the two gamma cameras. A method for imaging the anatomy of interest, such as the method depicted in FIG. 4, monitors the photon counts per pixel in regions of healthy tissue to control the acquisition. Such a method allows a sufficient amount of photon counts to be accumulated to generate an image, such as the image depicted in FIG. 5, wherein a lesion or cancerous tissue can be detected. As illustrated in FIGS. 6-8, additional biopsy cameras may be used to estimate the volume of a detected lesion. A method, such as the method depicted in FIG. 9, may calculate the absolute radioactivity of the lesion. The method may include differentiating the healthy tissue from the lesion, as illustrated in FIGS. 10-12, so that the method may correct for background noise and scatter. The method may further include correcting for photon attenuation, as depicted in FIG. 13. The method may also determine the location and depth of the lesion. A method, such as the method depicted in FIG. 14, may use the location and depth of the lesion to automatically perform a biopsy of the lesion. By calculating the absolute radioactivity of the lesion, a high confidence level that the lesion is malignant or benign can be established. For example, if the absolute radioactivity is high, the lesion could be considered as malignant with a confidence level as high as 85% or better. In such cases, a method such as the method depicted in FIG. 15 may include ablating the lesion instead of, or in addition to obtaining a biopsy sample. Additionally, a high confidence level that the lesion is malignant or benign may be used by the medical practitioner to decide whether to take a biopsy sample or not, and/or to decide how many biopsy samples to take and to select the biopsy taking method and tool.

Though an MBI system is described by way of example, it should be understood that the present techniques may also be useful when applied to images acquired using other NM imaging modalities. The present discussion of an MBI modality is provided merely as an example of one suitable imaging modality.

Further, though imaging of breasts is described by way of example, it should be understood that the present techniques may also be useful when applied to imaging other organs or body parts. The present discussion of breast imaging is provided merely as an example of one suitable imaging approach.

As used herein, the phrase "reconstructing an image" is not intended to exclude embodiments of the present disclosure in which data representing an image is generated but a viewable image is not. Therefore, as used herein the term "image" broadly refers to both viewable images and data representing a viewable image. However, many embodiments generate, or are configured to generate, at least one viewable image.

Figure 1:
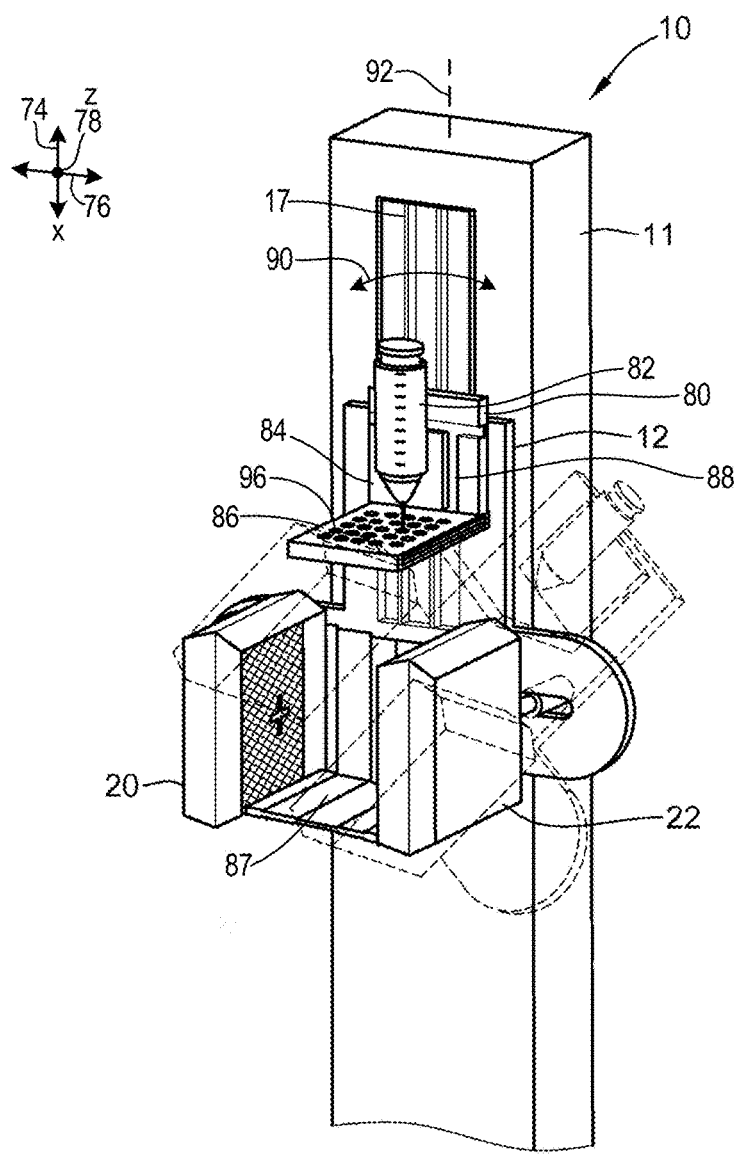
FIG. 1 is a front perspective view of an exemplary molecular imaging system in accordance with an embodiment.
Figure 2:
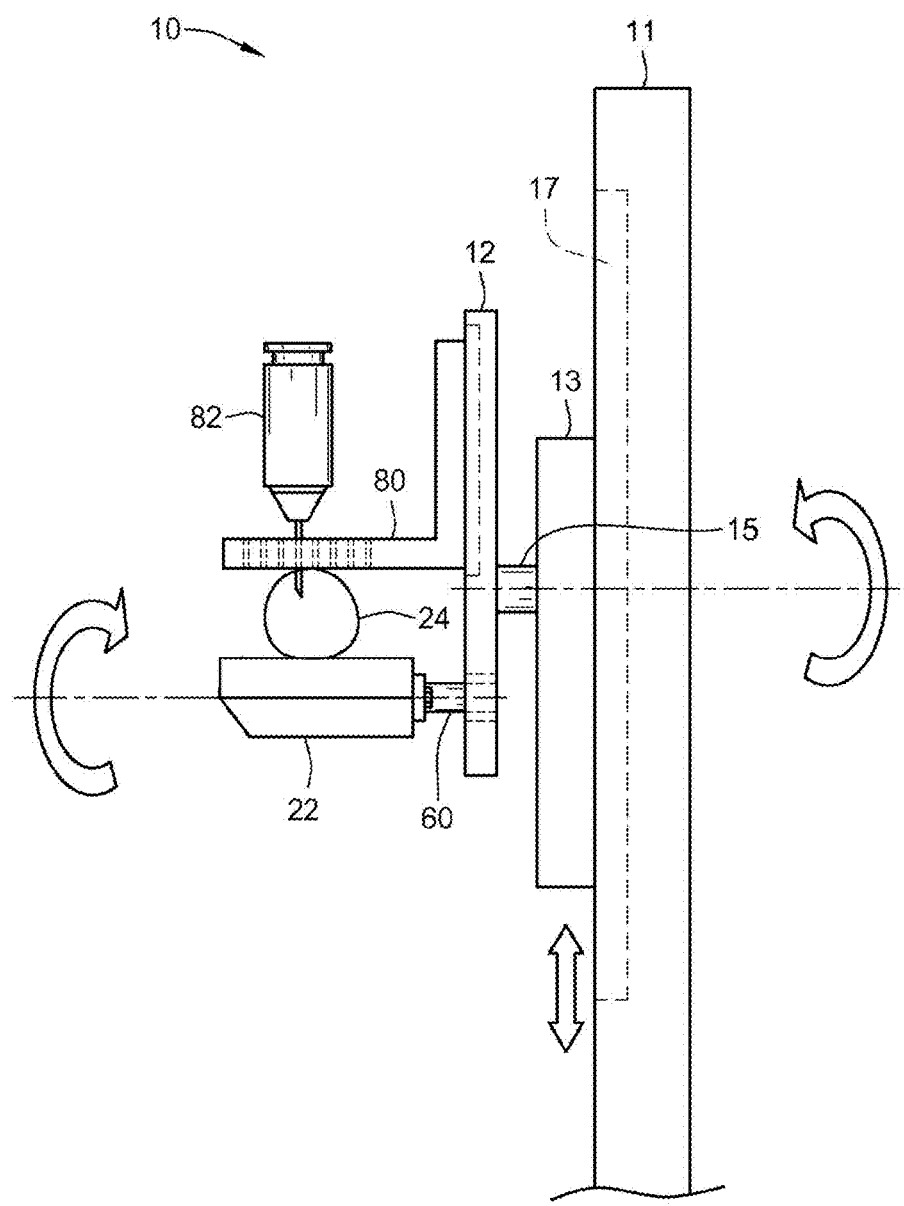
FIG. 2 is a side view of the imaging system show in FIG. 1.

FIG. 1 is a front perspective view of an exemplary molecular imaging system 10 illustrating a patient positioned for imaging in a first imaging position. FIG. 2 is a side view of the imaging system 10 shown in FIG. 1. In one example, the molecular imaging system 10 is configured as a standalone molecular imaging system. The molecular imaging system 10 may be mounted stationary by coupling the system 10 to a floor. Optionally the system 10 may include wheels (not shown) to enable system 10 to be portable. The molecular imaging system 10 includes a housing 11 and a gantry 12 that is rotatably coupled to the housing 11 via a carriage 13. The imaging system 10 also includes a first gamma camera 20, a second gamma camera 22, and a biopsy needle positioning device 80 that are coupled to the gantry 12. To facilitate imaging in various configurations, the gantry 12 is rotatable around the housing 11.

Referring to FIG. 2, the gantry 12 is coupled to the housing 11 via the carriage 13. The gantry is rotatably coupled to the carriage 13 via a pivot device 15. During operation, the carriage 13 is configured to move up and down along a pair of rails 17 to enable a patient to be imaged in a standing or sitting or bed position. Moreover, since the gamma cameras 20 and 22 and the biopsy needle positioning device 80 are rotatably coupled to the gantry 12 which is coupled to the carriage 13, the gamma cameras 20 and 22 and the biopsy needle positioning device 80 are also moveable along the pair of rails 17.

The gantry 12 is configured to pivot to a plurality of radial positions to position the gamma cameras 20 and 22 for imaging a patient. After the gantry 12 is positioned, the gantry 12 remains stationary during the imaging process as discussed below. Additionally, the first and second gamma cameras 20 and 22 are each positionable to perform imaging of an anatomy of interest 24 that is positioned between the first and second gamma cameras 20 and 22. During operation, the patient may be imaged by positioning the patient in a sitting position as shown in FIG. 1. In this imaging position, the gamma cameras 20 and 22 are adjusted vertically until the height of the gamma cameras 20 and 22 are sufficient to enable the patient to place a breast between the gamma cameras 20 and 22. More specifically, when the gamma cameras 20 and 22 are positioned at the proper imaging height, the patient is moved, via the movable table, into the field of view of the gamma cameras.

Figure 3:
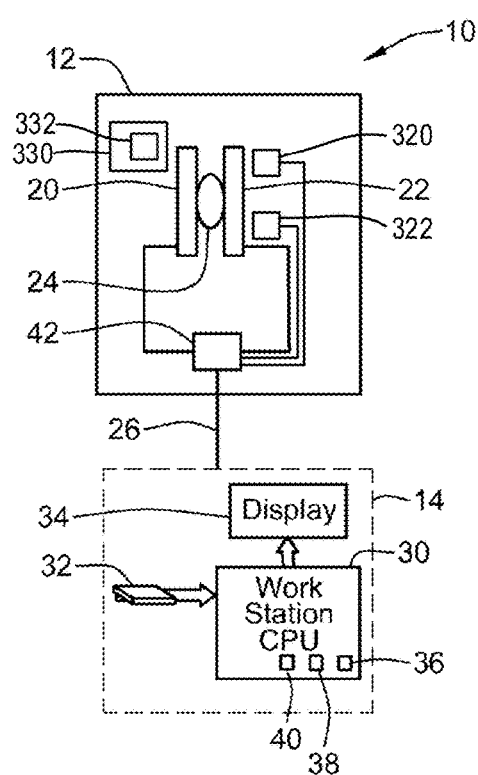
FIG. 3 is a schematic illustration of the exemplary molecular imaging system shown in FIGS. 1-2 in accordance with an embodiment.

FIG. 3 is a schematic illustration of an exemplary workstation 14 that may be included with system 10 to control image reconstruction processes. In one example, the operator workstation 14 is coupled to the housing 11, and thus is also coupled to the gantry 12 and the first and second gamma cameras 20 and 22. In one example, the gantry 12 is coupled to the operator workstation 14 via a communication link 26 (e.g., a hardwired communication link or wireless communication link). Optionally, the operator workstation 14 may be constructed as part of the housing 11.

The operation of the molecular imaging system 10 is controlled by the operator workstation 14. As shown in FIG. 2, the operator workstation 14 includes a general purpose or a dedicated computer 30, an input device 32, and a display 34. The computer 30 may include a processor 36 and a memory device 38. The memory device 38 may be embodied as a random access memory (RAM) and/or read only memory (ROM). The computer 30 further may include a storage device 40. The storage device 40 may be embodied as a hard disk drive or a removable storage such as a floppy disk drive, optical disk drive, USB memory, and the like. The storage device 40 may also be other similar means for loading computer programs or other instructions into the computer 30.

As used herein, the term "computer" may include any processor-based system including systems using controllers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer."

As discussed above, the operation of the molecular imaging system 10 is controlled from the operator workstation 14. More specifically, the processor 36 executes a set of instructions that are stored in one or more storage elements, e.g., the memory device 38 and/or the storage device 40. The set of instructions instruct the processor 36 to perform various functions. One exemplary function includes acquiring emission data from the gamma cameras 20 and 22 that is acquired from the anatomy of interest 24. More specifically, the set of instructions may include various commands that instruct the computer 30 as a processing machine to perform specific operations such as the methods and processes of the various embodiments described herein. For example, one set of instructions may instruct the processor 36 to perform a scan of the anatomy of interest 24 using the first and second gamma cameras 20 and 22 to acquire emission data. Another set of instructions may instruct the processor 36 to transmit the emission data from the first gamma camera 20 to the communication link 26 via a communication link 42 and to transmit emission data from the second gamma camera 22 to the communication link 26 via the communication link 42. The set of instructions may further include instructions to instruct the processor 36 to utilize the emission data to reconstruct an image of the anatomy of interest 24 and display the reconstructed image on a display, such as the display 34.

The set of instructions may be in the form of a software program. The software may be in various forms such as system software or application software. Further, the software may be in the form of a collection of separate programs, a program module within a larger program, or a portion of a program module. The software also may include modular programming in the form of object-oriented programming. The processing of input data by the processing machine may be in response to user commands, or in response to results of previous processing, or in response to a request made by another processing machine. As used herein, the terms "software" and "firmware" are interchangeable, and include any computer program stored in memory for execution by a computer, including RAM, ROM, EPROM, EEPROM, and non-volatile RAM (NVRAM). The above memory types are exemplary only, and are thus not limiting as to the types of memory usable for storage of a computer program.

During operation, the gamma cameras 20 and 22 may be configured to be repositioned from a first operational position to a second operational position. In some examples, the system 10 may include one or more motors (not shown) that are coupled to and move the gamma cameras 20 and 22 around a radial axis. In another example, the gamma cameras 20 and 22 may be repositioned manually by the operator. More specifically, the gamma cameras 20 and 22 may each be weighted and balanced and configured to enable the operator to disengage a mechanical or electromechanical clutch to permit manual repositioning of each respective gamma camera.

In one example, the gamma cameras 20 and 22 may be enabled to move in an x-direction 74, a y-direction 76, and optionally in a z-direction 78. Moving the gamma cameras 20 and 22 in the x-direction facilitates raising and lowering the gamma cameras 20 and 22, via the gantry 13, to enable to molecular imaging system 10 to accommodate a range of standing patients and/or sitting and/or reclining patients. Moving the gamma cameras 20 and 22 in the y-direction, via the gantry 12, facilitate moving the gamma cameras either closer together or further apart to enable the molecular imaging system 10 to accommodate different anatomies of interest having various sizes. As such, the gamma cameras 20 and 22 are each positionable along two or three linear and separate or linear and common axes. Moreover, the gamma cameras 20 and 22 and the gantry 12 are each rotatable to accommodate different imaging modes and patient anatomies.

As discussed above, the gamma cameras 20 and 22 may be either manually operated or motorized to enable the respective gamma cameras 20 and 22 to each be rotated in either a clock-wise direction or a counter-clockwise direction. As such, the gamma cameras 20 and 22 may be repositioned to perform imaging in an L-mode configuration, an H-mode configuration, or any other configuration between the L-mode and the H-mode configurations. The gamma cameras 20 and 22 may be in contact or separated and may have angles from 0° (parallel, in contact on an edge and beside each other) to 90° (contacting on an edge) to 180° (facing each other and not touching) with respect to each other.

In the L-mode configuration (not shown), the gamma camera 20 is substantially perpendicular to the gamma camera 22. In the H-mode configuration, shown in FIG. 1, the imaging face of the first gamma camera 20 is approximately parallel to and facing the imaging face of the second gamma camera 22. It should be realized that although only two operational modes are discussed, e.g., L-mode and H-mode, the gamma cameras 20 and 22 may be positioned in a plurality of operational positions within each of the L-mode and H-mode positions. In all cases, the precise relative position of the detectors can be known through previous calibration or mechanical, or electrical measurement or sensors, mounted on or mounted remotely from the system 10. The positions may be automatically recorded and used to present images and/or combine views, or guide biopsy with respect to features detectable in either or both detectors. In some examples, the molecular imaging system 10 may be limited to a single operational mode, such as H-mode. The methods described herein are described with regard to the molecular imaging system 10 operating in an H-mode, though it should be appreciated that the methods may be implemented with regard to other operational modes.

As mentioned above, the molecular imaging system 10 includes the biopsy needle positioning device 80 that is coupled to the gantry 12. The biopsy needle positioning device 80 may reposition a biopsy needle 82 to a first position in the L-mode configuration and to a second different position in the H-mode configuration. In some examples, the biopsy needle positioning device 80 includes a mounting plate 84 and a pressure plate 86 that is coupled to the mounting plate 84. As depicted, in some examples the mounting plate 84 is substantially perpendicular to the pressure plate 86. The mounting plate 84 includes a plurality of channels 88 that enable the biopsy needle 82 to move in the x-direction 74 and the y-direction 76. Moreover, the biopsy needle 82 is also repositionable along the z-axis 78. For example, the biopsy needle 82 may be moved along the z-axis closer to or further from the gantry 12 to enable larger and smaller anatomies of interest to be biopsied.

The biopsy needle positioning device 80 is also movable along an arcuate path 90. For example, during an L-mode imaging procedure, the biopsy needle positioning device 80 is movable along the arcuate path 90 to enable the biopsy needle 82 to be positioned at an approximately 0 degree position wherein the biopsy needle 82 is positioned at a centerline between the first and second gamma cameras 20 and 22. Additionally, the biopsy needle positioning device 80 is movable along the arcuate path 90 to enable the biopsy needle 82 to be positioned at approximately 45 degrees from the centerline 92, e.g., the biopsy needle is approximately parallel to either the gamma camera 20 or the gamma camera 22 when the molecular imaging system 10 is operated in the L-mode configuration. Any other line of approach to biopsy a lesion within the breast volume is also possible with computer positioning computation and guidance or control or visualization of the entry path superimposed on the gamma camera images of the breast and the target tissue.

As discussed above, the biopsy needle positioning device 80 also includes the penetrable pressure plate 86. In the L-mode configuration, the pressure plate 86 and the gamma cameras 20 and 22 together form a substantially triangular anatomy capture region 87. The anatomy capture region 87 is selectively sized to receive the anatomy of interest 24 therein. For example, the size of the anatomy capture region 87 may be increased to facilitate imaging a larger anatomy of interest by repositioning the gamma cameras 20 and 22 and the pressure plate 86 to form a larger triangular anatomy capture region 87. Moreover, to facilitate imaging a small anatomy of interest 24, the gamma cameras 20 and 22 and the pressure plate 86 may be repositioned to form a smaller triangular anatomy capture region 87. The pressure plate 86 may also be curved in some examples, and the anatomy capture region accordingly different. As well the plate may be constructed from foam or other tensile or stiff material to accomplish the same function.

The pressure plate 86 includes a plurality of penetrations, pores, virtual openings as between the weave of a fabric, or openings 96. In the exemplary embodiment, the openings 96 are arranged in rows along the y-axis and columns along the z-axis. Each opening 96 has a diameter that is sized to enable at least a portion of the biopsy needle 82 to be inserted therethrough. In one example, the pressure plate 86 is deformable to enable anatomies of interest having different sizes to be captured. In one example, the deformable immobilizing pressure plate 86 is positioned between the first and second gamma cameras 20 and 22 to secure the anatomy of interest 24 in a substantially fixed or immobilized position during the imaging procedure. In another example, the pressure plate 86 may include a single biopsy window 96 which may be positioned over a lesion for extracting a biopsy.

The gamma cameras 20 and 22 may include a Cadmium Zinc Telluride (CZT) detector array, an electronics device, and a collimator. More specifically, the gamma cameras 20 and 22 may be fabricated of a CZT semiconductor, or alternative compact detectors such as from CdTe or HgI or CsI or others. A photoconduction process within the CZT semiconductor generates electron-hole pairs in an interaction with gamma photons. The electrons and/or holes move toward respective electrodes of the electronics device, generating an output electrical signal comprising photon count, position, and energy data.

During operation, the patient is injected with a radiopharmaceutical that concentrates in known regions of the anatomy of interest and emits emission gamma rays. Subsequently, the anatomy of interest, in this case, the breast, 24 is positioned between the gamma cameras 20 and 22 as discussed above. The gamma rays emitted from the anatomy of interest 24 are collimated by the collimators of the gamma cameras to produce an image. The collimated gamma rays are then detected by the respective CZT detector arrays. The output from the CZT detector arrays are input to the respective electronic devices to be output as an electrical signal comprising photon count, position, and energy data. The outputs from the electronic devices are used to reconstruct or generate an image of the anatomy of interest 24.

In some examples, the molecular imaging system 10 further includes biopsy cameras 320 and 322. Biopsy cameras 320 and 322 may comprise CZT detectors similar to the gamma cameras 20 and 22, and thus may be similarly configured to acquire photon count, position, and energy data. To that end, biopsy cameras 320 and 322 may be configured to transmit acquired emission data to the operator workstation 14 (via communication link 26 and communication link 42) for generating biopsy images. These biopsy images may be processed to obtain additional data regarding a lesion within the anatomy of interest 24 which may be used for performing a biopsy.

Additionally, in some examples, the molecular imaging system 10 may include an ablation device 330. As discussed further herein with regard to FIG. 9, ablation device 330 may include an ablation probe 332 which may be inserted into the anatomy of interest to ablate an identified lesion.

Figure 4:
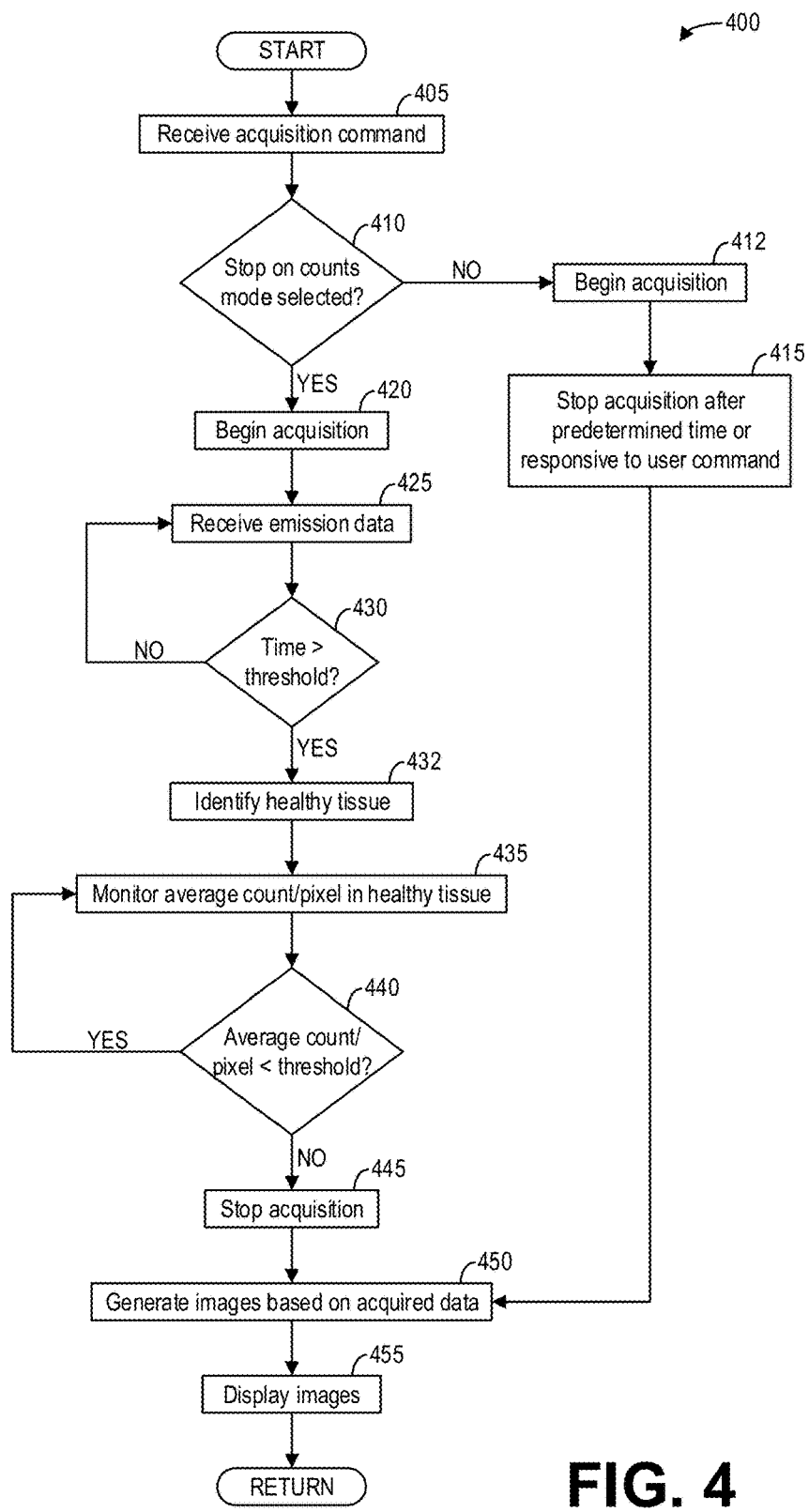
FIG. 4 shows a high-level flow chart illustrating an example method for molecular breast imaging in accordance with an embodiment.

FIG. 4 shows a high-level flow chart illustrating an example method 400 for molecular breast imaging in accordance with an embodiment. In particular, method 400 relates to controlling an acquisition based on measured counts per pixel. Method 400 is described herein with regard to the systems and components of FIGS. 1-3, though it should be appreciated that the method may be implemented with other systems and components without departing from the scope of the present disclosure. Method 400 may be carried out by a computer such as computer 30, and stored as executable instructions in non-transitory memory such as memory 38 or 40.

Method 400 begins at 405. At 405, method 400 receives an acquisition command. An acquisition command may be received, for example, via a user interface or input device 32, and initiates an acquisition. The acquisition command may be received after the anatomy of interest is properly positioned within the imaging system as described herein above, and furthermore after a radionuclide or radiotracer is administered to the patient. At 410, method 400 determines if a "stop on counts" mode is selected. More specifically, method 400 determines if a "stop on average background counts per pixel" mode is selected.

If a "stop on counts" mode is not selected ("NO"), method 400 proceeds to 412. At 412, method 400 begins an acquisition. At 415, method 400 stops the acquisition after a predetermined acquisition time or in response to a user command to end the acquisition. Method 400 then proceeds to 450, wherein method 400 generates images based on emission data acquired during the acquisition, and then to 455, wherein method 400 displays the generated images. Method 400 then ends.

However, referring again to 410, if the "stop on counts" mode is selected ("YES"), method 400 proceeds to 420. At 420, method 400 begins acquisition. At 425, method 400 receives emission data comprising photon counts, position, and energy from both gamma cameras.

At 430, method 400 determines if the elapsed time of the acquisition is greater than a time threshold. The elapsed time comprises the time elapsed since the acquisition began at 420. The time threshold may be predetermined to allow accumulation of an adequate number of photon counts to begin processing the emission data. In some examples, the time threshold may comprise two minutes. In other examples, the time threshold may comprise one minute. In yet other examples, the time threshold may comprise a time between one and two minutes. In some examples, the time threshold may be longer than two minutes, or shorter than one minute. It should be appreciated that the threshold time is shorter or less than the predetermined acquisition time at 415.

If the time is not greater than the threshold ("NO"), method 400 returns to 425 and continues receiving photon counts. In this way, the acquisition is allowed enough time to accumulate an adequate number of photon counts to begin monitoring the counts.

Once the elapsed time is greater than the time threshold ("YES"), method 400 proceeds to 432. At 423, method 400 identifies pixels corresponding to healthy tissue. In one example, to identify pixels corresponding to healthy tissue, method 400 may generate a data array comprising the photon counts for each pixel, and sort the data array based on counts per pixel. The method may then discard the lowest and the highest counts per pixel to avoid monitoring free space (e.g., in pixels with the lowest photon counts) as well as the lesion or other anatomical features having high uptake or increased scatter such as near the chest wall (e.g., in pixels with the highest photon counts). More specifically, the method may discard, for example, pixels having the lowest 10% of photon counts per pixel, and pixels having the highest 30% of photon counts per pixel from the data array. The remaining counts per pixel in the data array may then be assumed to correspond to healthy tissue.

After identifying the healthy tissue, method 400 continues to 435. At 435, method 400 monitors the average count per pixel in the healthy tissue. In one example, the method calculates the average counts per pixel of the remaining counts per pixel in the data array (i.e., in the pixels corresponding to healthy tissue). In one exemplary embedment, the healthy tissue averaged count rate is calculated by dividing the calculated healthy tissue average counts per pixel by the threshold time. A predicted acquisition time may be calculated by dividing the desired healthy tissue average counts per pixel by the calculated the healthy tissue averaged count rate. This predicted time may be: a) displayed to the user to inform him about the acquisition duration; b) used by the system as the predetermined stopping time for step 415 (in this case, the method continues to 415 with adjusted predetermined stopping time). Optionally, the user is alerted if the predicted time is outside a clinically acceptable range, for example shorter than half or longer than twice the predetermined stopping time. Optionally, the list of "healthy tissue pixel indexes" is retained.

At 440, method 400 determines if the average count per pixel is less than a threshold. The threshold comprises an adjustable average value at which enough emission data is accumulated for lesion detection. In one example, the threshold may comprise sixty counts per pixel.

If the average count per pixel is less than the threshold ("YES"), method 400 returns to 435 and continues monitoring the average count per pixel in the healthy tissue. In some examples, the method may estimate the remaining acquisition time based on the elapsed time and the average count per pixel, and the method may display the estimated remaining acquisition time. For example, if the threshold comprises sixty counts per pixel, and the current average count per pixel is twenty counts per pixel and the elapsed time is two minutes, the remaining time may comprise approximately six minutes until the average count per pixel reaches sixty counts per pixel. By displaying the estimated remaining time, for example via display 34, an operator may know how much time until the acquisition is complete. In some embodiments, the monitoring of average counts per pixel comprises repeating the process of sorting the pixel count array. In another embodiment average counts of pixels in the retained list of "healthy tissue pixel indexes" is recalculated at each step of monitoring after the list has been retained.

If the average count per pixel is equal to or greater than the threshold ("NO"), enough emission data has accumulated and so method 400 proceeds to 445. At 445, method 445 stops the acquisition. Optionally, the user is able to override the automatic termination of the acquisition by clicking on "stop now" or "continue acquisition" icon.

At 450, method 400 generates images based on the emission data acquired by both gamma cameras. More specifically, method 400 generates a first image based on emission data acquired by the first gamma camera (e.g., gamma camera 20) and a second image based on emission data acquired by the second gamma camera (e.g., gamma camera 22).

At 455, method 455 displays the generated images, for example via display 34, to an operator or practitioner. The operator or practitioner may then make a visual determination of whether a lesion is present in the images. In some examples, an additional method, such as the method described herein below with regard to FIG. 9, may be executed to automatically calculate the absolute radioactivity of a lesion, obtain a biopsy of the lesion, and/or ablate the lesion. Method 400 then ends.

Figure 5:
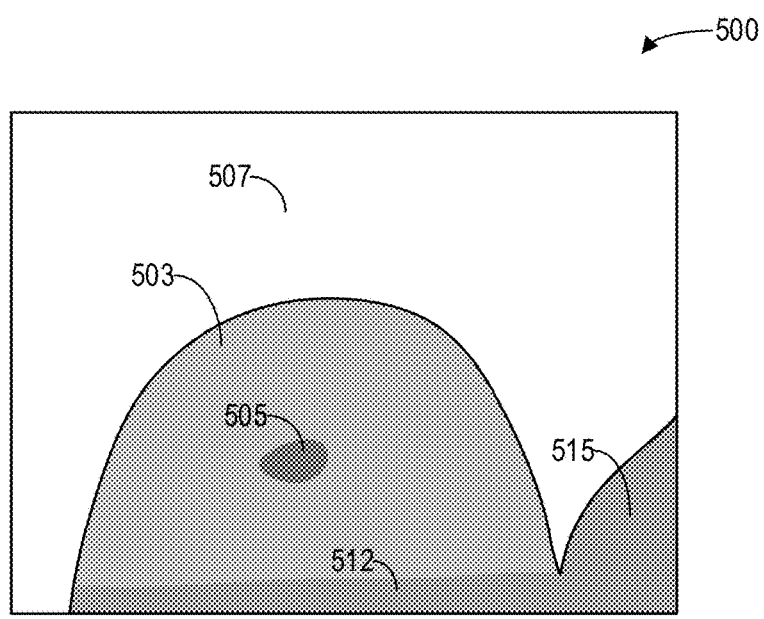
FIG. 5 shows an example image generated by the imaging system shown in FIGS. 1-3.

As an illustrative example, FIG. 5 shows an example image 500 generated by the imaging system shown in FIGS. 1-3. The image shows an anatomy of interest, in this example a breast, which comprises healthy tissue 503. As depicted, a lesion 505 is located within the healthy tissue 503. The image 500 further shows free space 507 (i.e., space away from the anatomy of interest and patient). The image 500 further includes the chest wall 512 and the axilla 515 of the patient.

As discussed above, a radiotracer is administered to the patient, and the radiotracer is carried by the bloodstream throughout the patient's body while emitting high-energy gamma photons which can be detected by the gamma cameras. Areas where the gamma ray emanations are higher than would be the case for normal healthy tissue in that area indicate an increased amount of uptake of the radiotracer in that tissue, possibly indicating cancerous tissue or a lesion.

Typically, cancerous tissue or lesions appears in the image as having 1.5 times more gamma counts per pixel than healthy tissue. As a result, a gamma camera may detect, say, 100 photon counts per pixel in regions of healthy tissue (such as healthy tissue 503), and 150 photon counts per pixel in regions of cancerous tissue (such as lesion 505). Under the assumption of statistical emission and detection of photons, the statistical variation in a pixel count number is approximately the square-root of the number of counts in said pixel (or a group of pixels). Thus, for the example given, a pixel having 100 counts is statistically significantly different than a pixel having 150 counts since $100+(100)^{\wedge}0.5=110$ counts is less than $150-(150)^{\wedge}0.5=137.8$ counts. Lower or higher count per pixel threshold values may be selected by the user or recommended by the manufacturer according to the lesion detectability confidence desired. Regions containing bone or arteries, such as the chest wall 512 and the axilla 515, may also exhibit increased uptake of the radiotracer, as depicted by the darker regions in the image 500. While a lesion is described as having 1.5 times more gamma counts per pixel than healthy tissue, it should be understood that this multiplier is exemplary, and that a lesion may have 1.2 to 3 times more gamma counts per pixel than healthy tissue. In fact, the uptake is 7 to 20 times higher per cc in a lesion, but the lesion is (assumed to be) small and thus occupies a small percentage of the breast thickness (e.g., as depicted in FIG. 6), so the planar image has much less contrast.

Thus, during a scan, once the average counts per pixel in the region of healthy tissue reaches the threshold, if there is a lesion within the anatomy of interest, the lesion should be visible because the region containing the lesion will have, on average, 50% more counts per pixel than the region of healthy tissue. As described above, by discarding the lowest counts per pixel, regions comprising free space 507 are not considered when calculating the average counts per pixel. Similarly, by discarding the highest counts per pixel, regions such as the axilla 515 and the chest wall 512 which are expected to have a higher uptake are not considered when calculating the average counts per pixel; further, if a lesion 505 is present, the lesion will also not be considered when calculating the average counts per pixel. In this way, the method 400 only monitors the average counts per pixel in the healthy tissue 503. The threshold average counts per pixel may be selected such that a lesion should be visible if present; that is, the average counts per pixel in regions containing a lesion should be greater than the average counts per pixel in regions of healthy tissue by a statistically significant margin. By controlling an acquisition based on the average counts per pixel in healthy tissue, the total time to accumulate enough emission data to detect a lesion may be decreased.

In some examples, the molecular imaging system may include one or more biopsy detectors for enhancing detection of a lesion. FIG. 6-7 show schematic diagrams illustrating example configurations of biopsy detectors in accordance with an embodiment. Specifically, FIG. 6 shows an example configuration 600 of two biopsy detectors 630 and 632. In some examples, the biopsy detectors 630 and 632 may be positioned in a slanted configuration with respect to the gamma cameras 620 and 622. As depicted, for example, the biopsy detectors 630 and 632 are rotated 30 degrees to the right and left of the vertical axis between the gamma cameras 620 and 622.

An anatomy of interest, in this example a breast, 605 is positioned between the gamma cameras 620 and 622 as described herein above such that a detected lesion 607 is positioned beneath a biopsy window 635 defined by pressure plate 625. Consequently, as depicted, the volume 638 wherein the field-of-view (FOV) 631 of the biopsy camera 630 intersects the FOV 633 of the biopsy camera 632 includes the lesion 607. By imaging the lesion 607 with the biopsy detectors 630 and 632, the specific location of the lesion 607 may be determined. For example, as depicted by the configuration 700 in FIG. 7, the regions of interest (ROI) 731 and 733 of the biopsy cameras 630 and 632, respectively, include the lesion 607. The volume 738 comprising the intersection of ROIs 731 and 733 approximately corresponds to the volume of the lesion 607. In some examples, the volume of the lesion 607 may be assumed to be the volume 738. In other examples, an ellipsoid or sphere may be fit within the volume 738 to approximate the volume of the lesion 607.

As illustrative examples, FIG. 8 shows example images 810 and 812 acquired using respective biopsy detectors, such as biopsy detectors 630 and 632. The image 810 may be generated from emission data acquired by the biopsy detector 630 over the FOV 631, for example, while the region 815 including the lesion 805 may comprise emission data acquired within the narrower ROI 731. Similarly, the image 812 may be generated from emission data acquired by the biopsy detector 632 over the FOV 633, while the region 817 including the lesion 805 may correspond to emission data acquired within the narrower ROI 733. As discussed above, the volume of the lesion 805 may be estimated using images such as 810 and 812, in addition to images generated from emission data acquired by the opposing gamma cameras.

Furthermore, in some examples, the method described herein above with regard to FIG. 4 may be applied to the biopsy cameras. For example, the method may monitor average counts per pixel in the healthy tissue 802 outside of the ROI 815 and 817, and may stop acquisition via the biopsy detectors based on the average counts per pixel in the healthy tissue 802 reaching a threshold count per pixel. In this way, acquisitions using the biopsy cameras may also be optimized for a particular patient and anatomy of interest. It should be noted that the method of "stop on average counts in healthy tissue" may be adapted to other type of cameras and other tissue types. The methods and systems described herein provide for the optimization of acquisition time when a searching for a lesion that may or may not exist in a relatively uniform healthy tissue. It also should be noted that while the example was given for a hot lesion (i.e., a lesion having higher uptake than the healthy issue), it may be adopted to "cold lesions" (i.e., lesions having lower uptake than the healthy issue) as well. The method may be extended to 3D imaging such as SPECT (Single Photon Emission Computed Tomography) and PET (Positron Emission Tomography) by performing 3D reconstruction and calculating the average count rate per healthy tissue voxel. Optionally, when the location of the organ of interest and sections that are to a large degree composed of healthy tissue are known, for example from an anatomical atlas, prior CT imaging, tissue segmentation, or other means, the pixels or voxels of healthy tissue may be determined from said known locations. It also should be realized that although large lesions may affect the accuracy of the computation, these large lesions are generally detectable at shorter time than the invention would suggest. While a user will not hesitate to terminate the acquisition when he/she identify a lesion in the FOV, the same user may be reluctant to terminate the acquisition when no lesion is detectable visually in the FOV.

Figure 9:
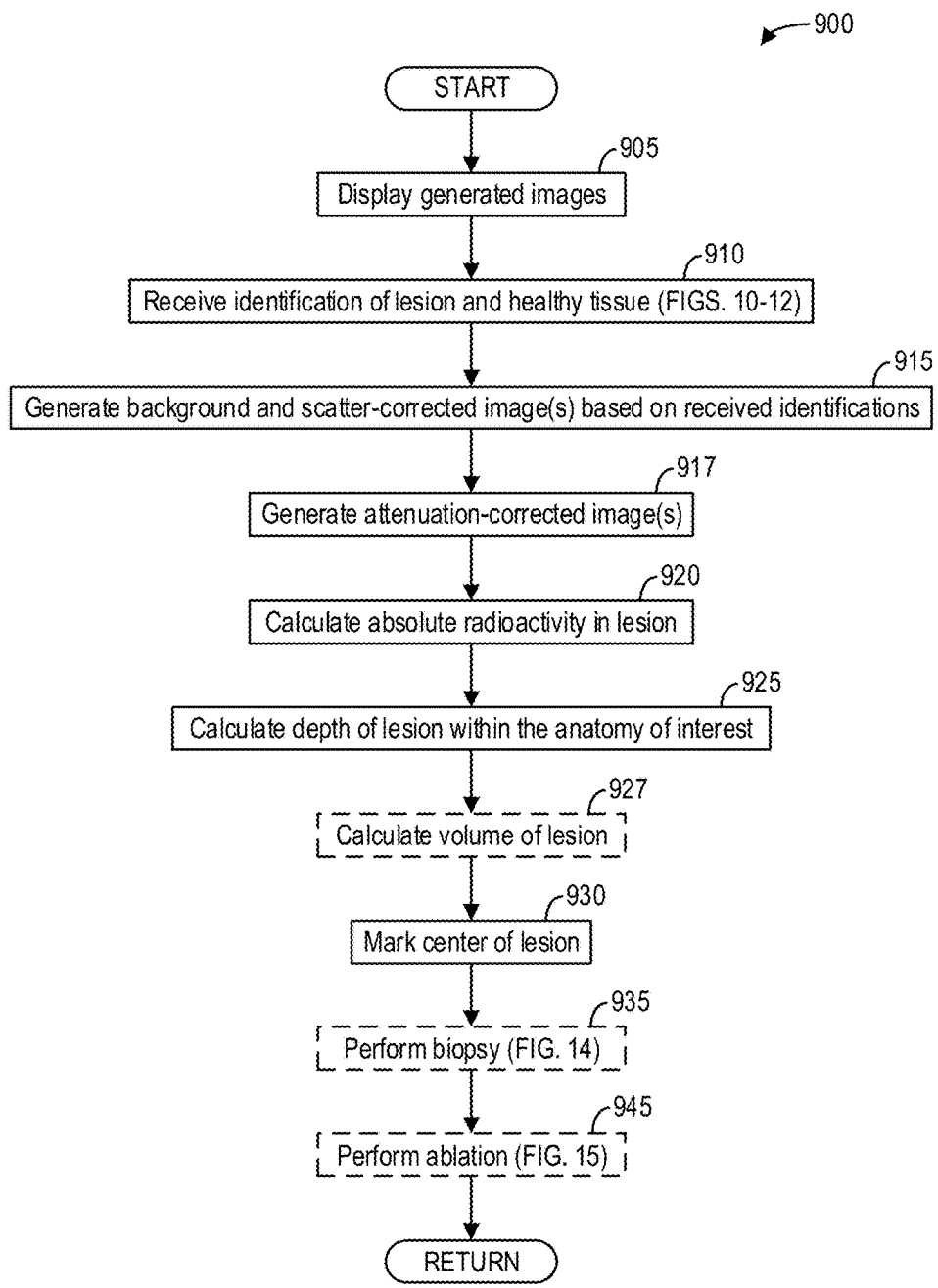
FIG. 9 shows a high-level flow chart illustrating an example method for molecular breast imaging in accordance with an embodiment.

FIG. 9 shows a high-level flow chart illustrating an example method 900 for molecular breast imaging in accordance with an embodiment. In particular, method 900 relates to absolute quantification of activity within a lesion. Method 400 is described herein with regard to the systems and components of FIGS. 1-3, though it should be appreciated that the method may be implemented with other systems and components without departing from the scope of the present disclosure. Method 400 may be carried out by a computer such as computer 30, and stored as executable instructions in non-transitory memory such as memory 38 or 40.

Method 900 begins at 905. At 905, method 900 displays generated images. In one example, method 900 displays a summed image comprising a combination of images generated from both gamma cameras. In another example, method 900 displays each separate image generated from both gamma cameras.

At 910, method 900 receives an identification of a lesion and an identification of healthy tissue. In one example, the operator may input, via input device 32 for example, an indication of the lesion and an indication of healthy tissue. For example, the computer (e.g., computer 30) may provide a virtual drawing tool that enables the operator to, via the input device, draw a circle or a freeform shape around the lesion in the reconstructed image, as well as a circle or a freeform shape around healthy tissue. The respective indications of the lesion and the healthy tissue thus comprise the shapes drawn around the lesion and the healthy tissue on the generated image(s). It should be understood that the indication of the healthy tissue should not include parts of the lesion, parts of other lesions, parts outside of the anatomy of interest, or "hot" scatter from the chest wall. In some examples, the indication of the healthy tissue may be drawn around the indication of the lesion. In such examples, the indication of the healthy tissue should be as symmetric around the indication of the lesion as possible.

To illustrate how indications of healthy tissue and the lesion should be input, FIG. 10 shows an example image 1000 of an anatomy of interest 1005 and a graph 1050 illustrating photon energy levels corresponding to slices of the example image 1000. More specifically, graph 1050 illustrates plots 1051, 1053, 1055, 1057, and 1059 of the energy distribution of photons that accumulated in corresponding slices 1011, 1013, 1015, 1017, and 1019, respectively.

As depicted by plot 1051, the highest energy distribution of photons are detected within the slice 1011 closest to the chest wall. This is due to the scattering of high-energy photons from the chest (e.g., the heart) and axilla wherein uptake of the radiotracer is high as expected. In contrast, the lowest energy distribution of photons (depicted by plot 1059) are detected within the slice 1019 furthest from the chest wall and only partially including the anatomy of interest. It should thus be appreciated that indications of the healthy tissue and the lesion may be selected from within a slice such that the scatter is similar.

As an illustrative example, FIG. 11 shows an example image 1100 of an anatomy of interest 1105 and a graph 1150 illustrating energy levels corresponding to selected regions of the example image 1150 in accordance with an embodiment. More specifically, the indication or selected region 1111 encloses the lesion 1107, while the indication or selected region 1113 encloses healthy tissue 1106 of the anatomy of interest 1105. The indications 1111 and 1113 may be drawn or otherwise selected by an operator, for example via a user interface or input device 32.

The plots 1151 and 1153 of graph 1150 illustrate the energy distribution of photons accumulated in the selected regions 1111 and 1113, respectively. Since both indications 1111 and 1113 are approximately the same distance from the chest wall, the energy distribution of photons are similar. Optionally, two regions of healthy tissue 1106 are drawn, one on each side of the region 1111 containing the lesion, and at approximately the same distance from the chest wall. It should be noted that NM images contains statistical photon noise, and healthy tissue is not completely uniform. Thus, in order to reduce the errors in estimating the properties of healthy tissue, a large area of healthy tissue is preferably sampled. As expected, the energy distribution 1151 is higher than the energy distribution 1153 due to the increased uptake of the radiotracer by the lesion 1107 in comparison to the healthy tissue 1106. Meanwhile, the energy distribution of photons from the healthy tissue 1106 may be assumed to comprise background and scatter noise. As described further herein, the background and scatter may be calculated based on the indication 1113 of the healthy tissue 1106, and this calculation may be subtracted from the indication 1111 of the lesion 1107.

Further, while square selections are depicted in FIG. 11, it should be appreciated that the indications of healthy tissue and the lesion may comprise any suitable shape. For example, in some examples the indications 1111 and 1113 may comprise circles, ovals, diamonds, rectangles, or any arbitrary shape.

Further still, in some examples the indication of healthy tissue may enclose the indication of the lesion. As an illustrative example, FIG. 12 shows an example image 1200 of an anatomy of interest 1205 with selected regions or indications for background, scatter, and attenuation correction in accordance with an embodiment. More specifically, the image 1200 includes an indication or selected region 1211 of a lesion 1207 within the anatomy of interest 1205. The image 1200 further includes an indication or selected region 1213 of healthy tissue. As depicted, the indication 1213 encloses or fully encompasses the indication 1211 of the lesion. The region between the indications 1211 and 1213 thus comprises a region of healthy tissue. This region may be referred to hereinafter as a healthy tissue zone or a background zone (as the background is calculated based on this region), while the region enclosed by the indication 1211 may be referred to as a lesion zone.

As depicted, the indications 1211 and 1213 comprise arbitrary shapes which may be drawn or otherwise input by an operator via a user interface or input device 32, for example. For example, the operator may, via the input device 32, draw the indications 1211 and 1213 on the image 1200 to indicate the lesion zone and the background or healthy tissue zone. The indication 1211 is carefully drawn to delineate the border of the lesion 1207 in the image 1200, while the indication 1213 is carefully drawn to encompass the indication 1211 such that only healthy tissue lies between the indications 1211 and 1213. In some examples, the operator may draw the indication 1213 in such a way as to ensure that the background zone does not include the chest wall, the lesion, muscles, the edges of the anatomy of interest 1205, or free space (e.g., the white area of image 1200 wherein no tissue is located).

Referring again to FIG. 9, after receiving the indications of healthy tissue and the lesion, method 900 proceeds to 915. At 915, method 900 performs background and scatter correction of the reconstructed images. In some examples, the method may first calibrate the image(s). For example, the image may be calibrated by multiplying the image by a system sensitivity factor, dividing by the injected dose, and applying a decay correction from the time of injection.

Then, to correct for scatter and background, it should be noted that the scatter and the background radiation in the lesion zone is similar to the scatter and background radiation around the lesion (i.e., in the healthy tissue zone), as discussed herein above with regard to FIGS. 10-12. In some examples, the scatter and the background radiation in and around the lesion may be approximated with a bilinear function.

In some examples, the background may be fit to a bilinear function. Specifically, in examples wherein the healthy tissue is identified at distances other than the lesion distance from the chest wall (for example, as depicted in FIG. 12), the background region between the indications of the healthy tissue and the lesion may be fit to a bilinear function, while in examples wherein the healthy tissue is identified at a same distance as the lesion from the chest wall (for example, as depicted in FIG. 11), the average distance to the chest wall is the same. The bilinear function is then subtracted from the pixel values. For example, for each pixel in the lesion zone, the method calculates a value from the bilinear function. In the entire zone, the method then subtracts the fit and make it non-negative. Alternatively, in the lesion zone, the method may subtract the fit and make it non-negative. The method may then display the background-corrected image.

More specifically, for pixels in the background zone, the method calculates:

$$x_{avg}=\text{Average}[x(i)], y_{avg}=\text{Average}[y(i)], \text{ and } z_{avg}=\text{Average}[z(i)],$$

where i is the pixel index in the background zone, z(i) is the photon count in pixel i, x(i) and y(i) are the x and y positions of pixel i, and Average[ ] is the usual arithmetic average. The method then calculates centered values:

$$X(i)=x(i)-x_{avg}, Y(i)=y(i)-y_{avg}, \text{ and } Z(i)=z(i)-z_{avg}.$$

The method then calculates equation coefficients. To that end, the method first defines a matrix M as:

$$M = \begin{pmatrix} M11 & M12 & M13 \\ M21 & M22 & M23 \\ M31 & M32 & M33 \end{pmatrix} = \begin{pmatrix} \text{Sum}[X(i)^2] & \text{Sum}[X(i)Y(i)] & \text{Sum}[X(i)] \\ \text{Sum}[X(i)^2] & \text{Sum}[Y(i)^2] & \text{Sum}[Y(i)^2] \\ \text{Sum}[X(i)] & \text{Sum}[Y(i)^2] & \text{Sum}[i] \end{pmatrix}$$

where Sum[i] comprises the number of pixels in the background zone. The method further defines several quantities:

$$V1 = \text{Sum}[X(i)Z(i)],$$

$$V2 = \text{Sum}[Y(i)Z(i)],$$

$$V3 = \text{Sum}[Z(i)],$$

and defines several additional matrices including these quantities:

$$MA = \begin{pmatrix} V1 & M12 & M13 \\ V2 & M22 & M23 \\ V3 & M32 & M33 \end{pmatrix};$$

$$MB = \begin{pmatrix} M11 & V1 & M13 \\ M21 & V2 & M23 \\ M31 & V2 & M33 \end{pmatrix};$$

$$MC = \begin{pmatrix} M11 & M12 & V1 \\ M21 & M22 & V3 \\ M31 & M32 & V3 \end{pmatrix}.$$

The method then calculates:

$$A = \frac{\text{Det}[MA]}{\text{Det}[M]}; B = \frac{\text{Det}[MB]}{\text{Det}[M]}, C = \frac{\text{Det}[MC]}{\text{Det}[M]},$$

where Det[x] comprises the determinant of x. With the above definitions and calculations, the method calculates the fitted background $Z_{fit}(i)$:

$$Z_{fit}(i) = AX(i) + BY(i) + C + Z_{avg}.$$

The fitted background is then subtracted from the pixel counts:

$$Z_{free}(i) = z(i) - Z_{fit}(i).$$

The method then calculates the minimum value:

$$Z_{min} = \text{Min}[Z_{free}(i)]Z_{min}.$$

and calculates a scatter and background-free calibrated image to be displayed to the operator:

$$Z_{show}(i) = Z_{free}(i) + Z_{min}.$$

The above process for background correction is separately applied to the data from each detector head or gamma camera. For the summed image (i.e., the combination of images from both gamma cameras), the method calculates:

$$Z_{freeSum}(i) = Z_{free}(i, \text{head } 1) + Z_{free}(i, \text{head } 2),$$

$$Z_{minSum} = \text{Min}[Z_{freeSum}(i)],$$

and then the method calculates the background-corrected summed image:

$$Z_{showSum}(i) = Z_{freeSum}(i) + Z_{minSum}.$$

In some examples, the method may then display the background-corrected image represented by $Z_{showSum}(i)$ to the operator via a display device.

After generating the scatter and background-corrected image as described above, the method then proceeds to 917. At 917, method 900 calculates an attenuation correction. To that end, in one example, the method first calculates the geometric mean:

$$\text{Geometric}(i) = \sqrt{Z_{free1}(i) \times Z_{free2}(i)},$$

where $Z_{free1}$ and $Z_{free2}$ respectively comprise the background-corrected images from the first and second detector heads.

In one example, the method corrects each pixel for attenuation based on breast thickness L and a total attenuation coefficient μ. For example, as illustrated by the schematic diagram 1300 illustrated in FIG. 13, the thickness of the breast 1305, which is compressed between gamma cameras 1320 and 1322, comprises the distance L between the gamma cameras 1320 and 1322. Further, the distance between the lesion 1307 and the gamma camera 1320 comprises a distance z, and so the distance between the lesion 1307 and the gamma camera 1322 comprises a distance L−z.

Thus, referring again to FIG. 9, in some examples, the method corrects each pixel for attenuation based on the measured breast thickness L and the known total attenuation coefficient μ:

$$\text{AttenCorrect}(i) = \text{Geometric}(i)/\text{Exp}\left[-\frac{\mu L}{2}\right].$$

The method may display the attenuation-corrected and background-free image represented by AttenCorrect(i) via a display device.

Alternatively, in some examples, a non-exponential attenuation correction may be applied. In such examples, the attenuation may be calculated based on the energy resolution of the detectors, a selected energy window, and collimator parameters of the detectors. Attenuation may behave non-exponentially due to small-angle Compton-scattered photons that pass through the collimators and fall within the energy window, which are thereby detected and indistinguishable from the direct radiation. The attenuation may be measured using the gamma cameras experimentally using a set of tissue slabs of different thicknesses. The results may then be fitted to a function F(z) where z is the distance such that the signal S(z) from a lesion at a depth z in the tissue is given by:

$$S(z) = A*F(z),$$

where A comprises the signal when the lesion is in air (i.e., no attenuation). Once the function F(z) is known, and the total breast thickness T is measured, the method calculates:

$$S1 = A*F1(z), S2 = A*F2(T-z),$$

where S1 and S2 comprise the counts measured in a first and a second detector head (e.g., gamma cameras 20 and 22) respectively, F1(z) and F2(T−z) comprise the attenuation functions for the first and second detector heads respectively for a lesion at a depth z from the first detector head. Note that F1 and F2 may be slightly different due to small variations in the properties of the first and second detector heads.

The method may then numerically solve the set of two equations given above for S1 and S2 for the two unknowns A and z, and generate attenuation-corrected image(s) based on the calculated parameters.

Continuing at 920, method 900 calculates absolute radioactivity in the lesion. More specifically, to calculate total uptake in the lesion, the method calculates:

TotalUptake=Sum[AttenCorrect($i$)].

In other words, the total uptake may be calculated by summing the counts of all pixels in the scatter-, background-, and attenuation-corrected image(s).

The malignancy of a lesion may be characterized by its total uptake above a similar-sized sample of healthy tissue. This represent a combination of excess uptake and lesion volume. After subtracting the healthy tissue from the lesion volume, what is left is only the excess uptake. After performing attenuation correction and normalization (by injected dose, isotope decay, and body weight or blood volume), absolute excess uptake is calculated. If the lesion is very small (e.g., a few image pixels), the malignancy may be judged by the sum of the absolute excess uptake. Similarly, when treatment efficacy is to be determined, the summed absolute excess uptake may be a preferable indicator as it will decrease if the lesion activity (uptake) or size will decrease, thus pointing to effective chemotherapy treatment. This is done on repeated visits. This indicator is easier to calculate accurately and thus more reliable than the currently used standard uptake value (SUV) used today.

As mentioned above, the bilinear function approach described above for background, scatter, and attenuation corrections as well as the absolute radioactivity calculation at 915, 917, and 920 are particularly applicable for embodiments wherein the indication of healthy tissue encloses the indication of the lesion (e.g., as depicted in FIG. 12). In embodiments wherein the indication of healthy tissue is adjacent to the indication of the lesion such that the indications are a same distance from the chest wall (e.g., as depicted in FIG. 11), the corrections and the absolute radioactivity calculation may alternatively be carried out based on the geometric mean. In such an embodiment, the geometric mean is first calculated for the entire image before subtracting the background using:

Geometric($i$)=$\sqrt{z(i,T)*z(i,B)}$ where i is the pixel index in the background zone, z(i,T) is the photon count in pixel i in the top detector, and z(i,B) is the photon count in pixel i in the bottom detector ("top" and "bottom" here are used for designating the first and second gamma cameras or detectors regardless of their relative positioning in relation to the floor).

An average background geometric mean (ABGM) is then computed by summing Geometric(i) in the range located in area of the image with comparable scatter radiation as the suspected lesion. For example, Geometric(i) values are summed for all pixels in selected region 1113 that encloses healthy tissue, and divided by the number of pixels in region 1113. Optionally, two zones of enclosing healthy tissue may be used for computing the ABGM, one on each side of the zone including the lesion, and in generally the same distance from the chest wall as the zone including the lesion. Thus, ABGM may be calculated using:

ABGM=Sum[Geometric($i$)]/$I$ where I is the total number of pixels in the zone (or zones) of healthy tissue used in the sum. The geometrical mean image is then corrected to form a corrected geometric image (CGI) by subtracting the value of ABGM from each of the Geometric(i) values:

CGI($i$)=Geometric($i$)−ABGM.

It should be noted that CGI(i) is close to zero in all healthy tissue pixels, and is substantially larger than zero for pixels in the lesion. A non-negativity requirement may be applied to by replacing any CGI(i) less than zero with the value zero.

Attenuation corrected values (ACV) may be then calculated as before by:

$$ACV(i) = CGI(i)/\mathrm{Exp}\left[-\frac{\mu L}{2}\right]$$

Total corrected uptake and other lesion parameters are similarly computed. For example, total corrected uptake in the lesion (TCUL) may be computed by calculating:

TCUL=Sum[ACV($i$)]

over all the pixels in the zone (e.g., zone 1111) containing the lesion. Alternatively, TCUL is computed by first computing the sum and then the attenuation correction:

$$TCUL = \mathrm{Sum}[CGI(i)]/\mathrm{Exp}\left[-\frac{\mu L}{2}\right]$$

Thus, the corrections and the total corrected uptake in the lesion may be obtained as described above for embodiments wherein the indications of healthy tissue and the lesion are adjacent and not overlapping.

At 925, method 900 calculates the depth of the lesion within the anatomy of interest. More specifically, for each gamma camera or detector head, the method calculates:

Z1($i$)=Max[0,$Z_{free1}(i)$],

Z2($i$)=Max[0,$Z_{free2}(i)$], where $Z_{free1}$ and $Z_{free2}$ respectively comprise the background-corrected images from the first and second detector heads. The method then calculates, for each detector head or gamma camera:

Tot1=Sum[Z1($i$)],

Tot2=Sum[Z2($i$)].

After subtracting the scatter and background,

Tot1=TotalUptake*Exp[−$\mu$*$z$],

Tot2=TotalUptake*Exp[−$\mu$*($L-z$)], and so it follows that:

ln [TotalUptake/Tot1]=−$\mu$*$z$, ln [TotalUptake/Tot2]=−$\mu$*($L-z$), where L and z are the distances described herein above with regard to FIG. 13. Thus, to estimate the depth of the lesion, the method calculates two estimates from each detector head or gamma camera:

Estimation1=ln [TotalUptake/Tot1]/$\mu$,

Estimation2=$L$+ln [TotalUptake/Tot2]/$\mu$.

From these estimations, the method calculates the estimated depth by calculating the arithmetic mean of the estimations:

EstimatedDepth=(Estimation1+Estimation2)/2.

Continuing at 927, in some examples, method 900 optionally calculates the volume of the lesion. The volume of the lesion may be calculated as described herein above with regard to FIGS. 6-7. Specifically, the volume of the lesion may be calculated or estimated based on the two opposing views provided by the gamma cameras in addition to the two views provided by the pair of biopsy detectors. An upper limit to the volume comprises the volume 738 within the intersections of parallel projections of the ROI defined in the two slanted views 731 and 733 and the two opposing views of the gamma cameras. In some examples, the volume may be estimated by fitting an ellipsoid or a sphere, for example, into the volume 738. In some examples, estimation of lesion volume may not be performed as such an estimation may be inaccurate due to limited camera resolution (e.g., the lesion is usually too small to be truly resolved by the camera, for example, a 5-10 mm lesion imaged by a camera having 2.5 mm pixels and 7 mm collimator resolution), and further because the thickness and shape of the lesion is unknown.

Continuing at 930, method 900 marks the center of the lesion. In some examples, marking the center of the lesion comprises estimating the center of the lesion based, as a non-limiting example, on the calculated depth of the lesion and/or the estimated volume of the lesion. The estimated center of the lesion may thus be used to determine where to insert a biopsy needle and/or an ablation probe as described further herein below.

Additionally or alternatively, marking the center of the lesion may comprise physically attaching a radioactive marker to the lesion. The radioactive marker may be fixedly attached to the center of the lesion such that the lesion may be easily identified by an imaging system during subsequent imaging procedures. In some instances, dyes or isotope dye mixtures are applied to the lesion for subsequent identification.

Figure 14:
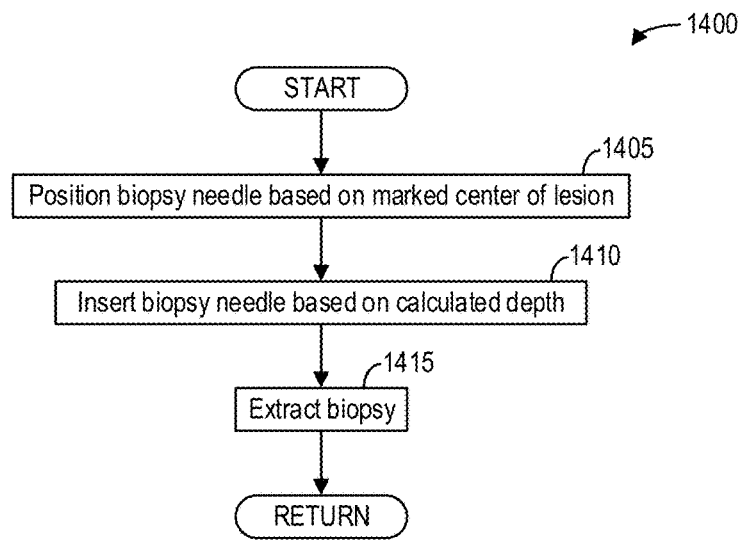
FIG. 14 shows a high-level flow chart illustrating an example method for performing a biopsy in accordance with an embodiment.

At 935, method 900 optionally performs a biopsy. As an illustrative example, FIG. 14 shows a high-level flow chart illustrating an example method 1400 for performing a biopsy according to an embodiment. Method 1400 may comprise a subroutine of method 900, though it should be appreciated that the method may be implemented with other systems and methods without departing from the scope of the present disclosure.

Method 1400 begins at 1405. At 1405, method 1400 positions the biopsy needle based on the marked center of the lesion. At 1410, method 1400 inserts the biopsy needle into the anatomy of interest based on the calculated depth. At 1415, method 1400 extracts a biopsy sample. Method 1400 then returns. The biopsy sample may be sent to a pathology laboratory for testing.

Referring again to FIG. 9, after optionally performing a biopsy, method 900 may continue to 945. Alternatively, if a biopsy is not performed, method may optionally continue directly to 945 from 930. At 945, method 900 optionally performs ablation. In some examples, ablation may be automatically performed responsive to the absolute activity calculated at 920. For example, if the absolute activity of the lesion indicates that the lesion is malignant with a high confidence level (e.g., 80% or more), the patient may opt for the lesion to be ablated during the procedure. An ablation device, such as the ablation device 330 of the imaging system 10, may be automatically positioned and controlled to perform ablation of the lesion. To that end, the computer 30 may control the ablation device 330 to insert the ablation probe 332 into the anatomy of interest, and then to ablate the lesion. The ablation device may utilize any suitable ablation technique, including but not limited to laser ablation, cryo-ablation, radiofrequency ablation, chemoablation, fulguration, rotoablation, genetic ablation, thermal ablation, and so on.

Figure 15:
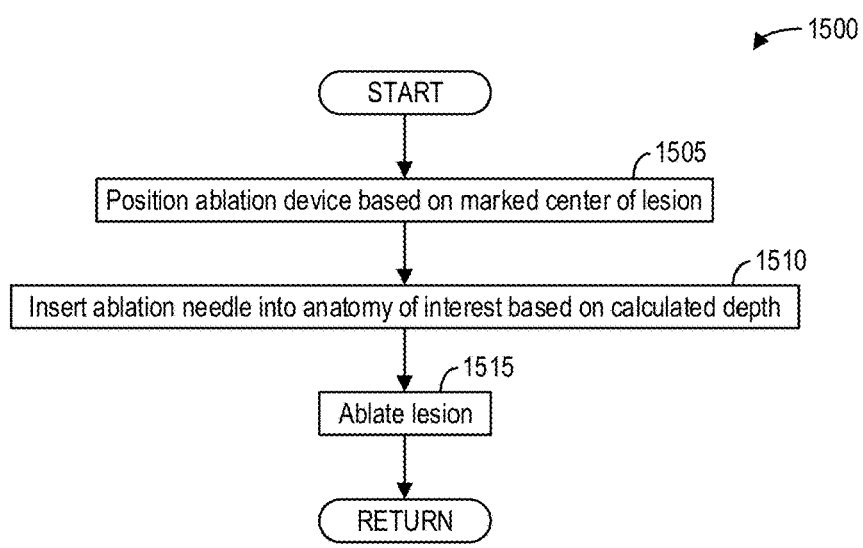
FIG. 15 shows a high-level flow chart illustrating an example method for automatically performing an ablation in accordance with an embodiment.

As an illustrative example, FIG. 15 shows a high-level flow chart illustrating an example method 1500 for performing ablation according to an embodiment. Method 1500 may comprise a subroutine of method 900, though it should be appreciated that the method may be implemented with other methods and systems without departing from the scope of the present disclosure.

Method 1500 begins at 1505. At 1505, method 1500 positions the ablation device based on the marked center of the lesion. For example, the ablation device may be positioned over the biopsy window positioned over the center of the lesion. At 1510, method 1500 inserts the ablation probe into the anatomy of interest based on the calculated depth. In examples wherein a biopsy is performed, the ablation probe may be inserted through a same channel as the biopsy needle. At 1515, method 1500 ablates the lesion. For example, the ablation probe may comprise a cryogenic-ablation probe, thermal ablation probe, radiofrequency ablation probe, or another probe which ablates the surrounding tissue within a specified distance from the end of the probe. Ablating the lesion may thus comprise activating the ablation probe such that the ablation probe ablates the lesion. As discussed above, any suitable ablation technique may be used to ablate the lesion, including but not limited to laser ablation, cryo-ablation, radiofrequency ablation, chemoablation, fulguration, rotoablation, genetic ablation, and so on. Method 1500 then ends.

Referring again to FIG. 9, after optionally performing ablation, method 900 may then end.

Thus, a technique for providing efficient diagnosis and treatment of breast cancer is disclosed. The technique includes a combined diagnostic-biopsy-treatment medical device for treating a patient having high risk of breast cancer. The patient is injected with a radiopharmaceutical agent having high specificity for breast cancer. If a lesion is detected, and determined to have high probability of being malignant, a biopsy unit is attached and configured for taking a biopsy sample. Further, a depth scan is performed to determine three dimensional (3D) location of the detected lesion, for example using the biopsy detectors described herein above.

Once location of the lesion is known, at least one biopsy sample is taken under local anesthesia and sent to pathology laboratory for further testing. According to an embodiment of the technique, a radio-opaque staple is placed at the site of the lesion. Further, an ablation probe is placed via a same cavity made for a biopsy needle and the lesion is ablated. The ablation probe may be a cryogenic-ablation probe, thermal, radiofrequency (RF) or another ablation probe. Accordingly, the lesion is treated in the same surgical session with the biopsy, before pathology results are back from the pathology laboratory, which may take many hours to a few days.

Advantageously, the technique described herein requires a single session for diagnosis and treatment of the lesion. As a result, the technique reduces patient recovery time, cost of breast cancer diagnosis and treatment and decreases morbidity by lowering tumor growth and spread rate in the body of the patient. Also, the technique described herein prevents delay in treatment and psychological stress due to elimination of dependency on long duration waiting for biopsy reports A technical effect of the disclosure may include the monitoring of average counts per pixel during an acquisition. Another technical effect of the disclosure may include the controlling of an acquisition in real-time based on the average counts per pixel. Another technical effect of the disclosure may include the automatic calculation of the absolute activity of a lesion within an anatomy of interest. Yet another technical effect of the disclosure may include the automatic acquisition of a biopsy. Another technical effect of the disclosure may include the automatic ablation of a lesion based on a calculated absolute activity of the lesion. Yet another technical effect of the disclosure may include the correction of background, scatter, and attenuation effects in an image. Another technical effect of the disclosure may include the displaying of an image corrected for background, scatter, and attenuation effects. Another technical effect of the disclosure may include correcting an image for attenuation without the assumption of exponential attenuation.

In one embodiment, a method for nuclear medicine imaging comprises: during an acquisition of emission data from an anatomy of interest, calculating an average counts per pixel; and responsive to the average counts per pixel reaching a threshold, automatically stopping the acquisition. The method calculates the average counts per pixel in non-target tissue.

In a first example of the method, calculating the average counts per pixel in non-target tissue comprises calculating the average counts per pixel for pixels corresponding to healthy tissue in the anatomy of interest. In a second example of the method optionally including the first example, the method further comprises automatically identifying the pixels corresponding to the healthy tissue by sorting a list of counts per pixel of the emission data. In a third example of the method optionally including one or more of the first and second examples, automatically identifying the pixels corresponding to the healthy tissue further comprises discarding a bottom percentage and a top percentage of the sorted list, and calculating the average counts per pixel comprises calculating an average of the remaining counts per pixel in the sorted list. In a fourth example of the method optionally including one or more of the first through third examples, the calculating is performed after a threshold time elapsing from a start of the acquisition. In a fifth example of the method optionally including one or more of the first through fourth examples, the method further comprises generating one or more images based on the emission data. In a sixth example of the method optionally including one or more of the first through fifth examples, the method further comprises displaying, via a display device, the one or more images. In a seventh example of the method optionally including one or more of the first through sixth examples, the threshold is adjustable by an operator.

In another embodiment, a method for nuclear medicine imaging comprises: calculating background, scatter, and attenuation corrections of an image of a lesion in an anatomy of interest based on an indication of healthy tissue in the anatomy of interest and an indication of the lesion; and calculating absolute radioactivity in a lesion based on the background, scatter, and attenuation corrections of the image.

In a first example of the method, the background and scatter corrections are calculated by fitting a bilinear function to a background zone defined by the indication of the healthy tissue, and subtracting the bilinear function from the indication of the lesion. In a second example of the method optionally including the first example, the attenuation correction is calculated by applying an exponential correction to a background- and scatter-corrected image. In a third example of the method optionally including one or more of the first and second examples, calculating the absolute radioactivity comprises summing photon counts over pixels of the image within the indication of the lesion after applying the background, scatter, and attenuation corrections to the pixels. In a fourth example of the method optionally including one or more of the first through third examples, the method further comprises receiving the indication of the lesion and the indication of the healthy tissue via an input device. In a fifth example of the method optionally including one or more of the first through fourth examples, the indication of the healthy tissue fully encompasses the indication of the lesion.

In yet another embodiment, a nuclear medicine system comprises: a detector configured to detect photons emanating from an anatomy of interest; and a computer communicatively coupled to the detector and configured with executable instructions in non-transitory memory that when executed cause the computer to: during an acquisition, via the detector, of emission data from an anatomy of interest, calculate an average counts per pixel in non-target tissue; and responsive to the average counts per pixel reaching a threshold, automatically stop the acquisition.

In a first example of the system, calculating the average counts per pixel in the non-target tissue comprises calculating the average counts per pixel for pixels corresponding to healthy tissue of the anatomy of interest. In a second example of the system optionally including the first example, the pixels corresponding to the healthy tissue are automatically determined. In a third example of the system optionally including one or more of the first and second examples, the system further comprises a display device communicatively coupled to the computer, and the computer is further configured with executable instructions in the non-transitory memory that when executed cause the computer to: after the acquisition, display, via the display device, an image of the anatomy of interest generated based on the emission data; receive, via an input device communicatively coupled to the computer, indications of healthy tissue and a lesion within the anatomy of interest; calculate background, scatter, and attenuation corrections of the image based on the received indications; and display, via the display device, a background-, scatter-, and attenuation-corrected image generated based on the corrections. In a fourth example of the system optionally including one or more of the first through third examples, the computer is further configured with executable instructions in the non-transitory memory that when executed cause the computer to automatically calculate absolute activity of the lesion based on the background-, scatter-, and attenuation-corrected image. In a fifth example of the system optionally including one or more of the first through fourth examples, the system further comprises an ablation probe, and the computer is further configured with executable instructions in the non-transitory memory that when executed cause the computer to perform ablation, via the ablation probe, of the lesion responsive to the absolute activity above a threshold.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for nuclear medicine imaging, comprising:
during an acquisition of emission data from an anatomy of interest, calculating an average counts per pixel in non-target tissue; and
responsive to the average counts per pixel reaching a threshold, automatically stopping the acquisition.

2. The method of claim 1, wherein calculating the average counts per pixel in non-target tissue comprises calculating the average counts per pixel for pixels corresponding to healthy tissue in the anatomy of interest.

3. The method of claim 2, further comprising automatically identifying the pixels corresponding to the healthy tissue by sorting a list of counts per pixel of the emission data.

4. The method of claim 3, wherein automatically identifying the pixels corresponding to the healthy tissue further comprises discarding a bottom percentage and a top percentage of the sorted list, and wherein calculating the average counts per pixel in corresponding to healthy tissue in the anatomy of interest. the non-target area comprises calculating an average of the remaining counts per pixel in the sorted list.

5. The method of claim 1, wherein the calculating is performed after a threshold time elapsing from a start of the acquisition.

6. The method of claim 1, further comprising generating one or more images based on the emission data.

7. The method of claim 6, further comprising displaying, via a display device, the one or more images.

8. The method of claim 1, wherein the threshold is adjustable by an operator.

9. A nuclear medicine system, comprising:
a detector configured to detect photons emanating from an anatomy of interest;
a computer communicatively coupled to the detector and configured with executable instructions in non-transitory memory that when executed cause the computer to:
during an acquisition of emission data from [[an]]the anatomy of interest, calculate an average counts per pixel in non-target tissue; and
responsive to the average counts per pixel reaching a threshold, automatically stop the acquisition.

10. The system of claim 9, wherein calculating the average counts per pixel in the non-target tissue comprises calculating the average counts per pixel for pixels corresponding to healthy tissue of the anatomy of interest.

11. The system of claim 10, wherein the pixels corresponding to the healthy tissue are automatically determined.

12. The system of claim 9, further comprising a display device communicatively coupled to the computer, wherein the computer is further configured with executable instructions in the non-transitory memory that when executed cause the computer to:
after the acquisition, display, via the display device, an image of the anatomy of interest generated based on the emission data;
receive, via an input device communicatively coupled to the computer, indications of healthy tissue and a lesion within the anatomy of interest;
calculate background, scatter, and attenuation corrections of the image based on the received indications; and
display, via the display device, a background-, scatter-, and attenuation-corrected image generated based on the corrections.

13. The system of claim 12, wherein the computer is further configured with executable instructions in the non-transitory memory that when executed cause the computer to automatically calculate absolute activity of the lesion based on the background-, scatter-, and attenuation-corrected image.

14. The system of claim 13, further comprising an ablation probe, wherein the computer is further configured with executable instructions in the non-transitory memory that when executed cause the computer to perform ablation, via the ablation probe, of the lesion responsive to the absolute activity above a threshold.

* * * * *